(12) United States Patent
Okumu et al.

(10) Patent No.: US 9,968,621 B2
(45) Date of Patent: May 15, 2018

(54) PARENTERAL COMPOSITIONS OF CELECOXIB

(71) Applicant: Dr. Reddy's Laboratories Ltd., Hyderabad (IN)

(72) Inventors: Franklin Okumu, Morristown, NJ (US); Jan-Jon Chu, Carlsbad, CA (US); Julie Ann Webb, San Diego, CA (US); Rafael Anthony Sabino, San Diego, CA (US); Andrew Xian Chen, San Diego, CA (US)

(73) Assignee: Dr. Reddy's Laboratories Ltd. (IN)

( * ) Notice: Subject to any disclaimer, the term of this patent is extended or adjusted under 35 U.S.C. 154(b) by 0 days. days.

(21) Appl. No.: 15/240,577

(22) Filed: Aug. 18, 2016

(65) Prior Publication Data

US 2016/0354390 A1 Dec. 8, 2016

Related U.S. Application Data

(62) Division of application No. 14/619,634, filed on Feb. 11, 2015, now Pat. No. 9,446,056.

(60) Provisional application No. 61/938,338, filed on Feb. 11, 2014.

(51) Int. Cl.
| | |
|---|---|
| *A61K 31/635* | (2006.01) |
| *A61K 47/24* | (2006.01) |
| *A61K 9/00* | (2006.01) |
| *A61K 9/107* | (2006.01) |
| *A61K 47/44* | (2017.01) |
| *A61K 31/415* | (2006.01) |
| *A61K 47/14* | (2017.01) |
| *A61K 47/10* | (2017.01) |

(52) U.S. Cl.
CPC .......... *A61K 31/635* (2013.01); *A61K 9/0019* (2013.01); *A61K 9/107* (2013.01); *A61K 9/1075* (2013.01); *A61K 31/415* (2013.01); *A61K 47/14* (2013.01); *A61K 47/24* (2013.01); *A61K 47/44* (2013.01); *A61K 47/10* (2013.01)

(58) Field of Classification Search
CPC .... A61K 31/635; A61K 47/24; A61K 9/0019; A61K 9/1075; A61K 47/44; A61K 31/415; A61K 9/107; A61K 47/14; A61K 47/10

See application file for complete search history.

(56) References Cited

U.S. PATENT DOCUMENTS

| | | | |
|---|---|---|---|
| 5,466,823 | A | 11/1995 | Talley et al. |
| 5,496,818 | A | 3/1996 | Schaupp et al. |
| 6,007,826 | A | 12/1999 | Benita et al. |
| 6,383,471 | B1 | 5/2002 | Chen et al. |
| 6,451,339 | B2 | 9/2002 | Patel et al. |
| 6,495,164 | B1 * | 12/2002 | Ramstack ............ A61K 9/0019 424/484 |
| 6,589,557 | B2 | 7/2003 | Straub et al. |
| 6,589,973 | B1 | 7/2003 | Patel et al. |
| 7,695,736 | B2 | 4/2010 | Kararli et al. |
| 8,298,568 | B2 | 10/2012 | Bague et al. |
| 2005/0191343 | A1 | 9/2005 | Liang |
| 2009/0263486 | A1 | 10/2009 | Prestidge et al. |
| 2011/0065677 | A1 * | 3/2011 | Lichtenberger ........ A61K 9/107 514/162 |
| 2014/0112978 | A1 * | 4/2014 | Su ........................... C07C 67/10 424/450 |

FOREIGN PATENT DOCUMENTS

| | | |
|---|---|---|
| WO | 2008032327 A2 | 3/2008 |
| WO | 2008051186 A2 | 5/2008 |
| WO | 2008077823 A1 | 7/2008 |
| WO | 2008/113177 A1 | 9/2008 |
| WO | 2013010400 A1 | 1/2013 |

OTHER PUBLICATIONS

Ketan Hippalgaonkar, et al, Injectable Lipid Emulsions—Advancements, Opportunities and Challenges, 11 AAPS Pharm. Sci. Tech. 1526 (2010).*
Neal Davies, et al, Clinical Pharmacokinetics and Pharmacodynamics of Celecoxib a Selective Cyclo-Oxygenase-2 Inhibitor, 38 Clin. Pharmacokinet. 225 (Year: 2000).*
Yasushi Shono, et al, Prediction of food Effects on the Absorption of Celecoxib Based in Biorelevant Dissolution Testing Coupled with Physiological Based Pharmacokinetic Modeling, 73 Eur. J Pharmaceut. Biopharmaceut. 107 (Year: 2009).*
Brophy, James M., "Celecoxib and cardiovascular risks", Expert Opin. Drug Saf. (2005) 4(6): 1005-1015.
International Search Report and Written Opinion for Application No. PCT/US2015/015379 dated Apr. 22, 2015.
Neal Davies, et al, Clinical Pharmacokinetics and Pharmacodynamics of Celecoxib a Selective Cyclo-Oxygenase-2 Inhibitor, 38 Clin. Pharmacokinet. 225 (2000).
Wolfgang Koppert, et al, The Cyclooxygenase Isozyme Inhibitors Parecoxib and Paracetamol Reduce Central Hyperalgesia in Humans, 108 Pain 148 (2004).
Yalkowsky, S.H., et al., Formulation-Related Problems Associated with Intravenous Drug Delivery, Journal of Pharmaceutical Sciences, vol. 87, No. 7, Jul. 1998.
Yasushi Shona, et al, Prediction of food Effects on the Absorption of Celecoxib Based in Biorelevant Dissolution Testing Coupled with Physiological Based Pharmacokinetic Modeling, 73 Eur. J Pharmaceut. Biopharmaceut. 107 (2009).

* cited by examiner

*Primary Examiner* — Sean M Basquill
(74) *Attorney, Agent, or Firm* — Lerner, David, Littenberg, Krumholz & Mentlik, LLP

(57) ABSTRACT

Parenteral (injectable) celecoxib emulsions and nanoemulsions are disclosed as are their use to treat pain in patients so afflicted. The emulsions are generally oil in water emulsions often comprised of an oil phase including an oil and a lecithin wherein the mean droplet size of the discontinuous oil phase is about 200 nanometers or less.

15 Claims, No Drawings

PARENTERAL COMPOSITIONS OF CELECOXIB

CROSS-REFERENCE TO RELATED APPLICATIONS

This application a divisional application of U.S. patent application Ser. No. 14/619,634, filed Feb. 11, 2015, which claims the benefit of the filing date of U.S. Provisional Patent Application No. 61/938,338 filed Feb. 11, 2014, the disclosures of which are hereby incorporated herein by reference.

FIELD OF THE INVENTION

The present invention relates to parenteral composition of celecoxib thereof and process of preparing and method of using said parenteral composition of celecoxib.

BACKGROUND OF THE INVENTION

Non-steroidal anti-inflammatory drugs (NSAID) are generally used for treatment of acute pain, inflammatory pain, visceral pain, breakthrough pain, nociceptive pain, neuropathic pain, dysmenorrhea, post-surgical pain, acute postpartum pain, postoperative pain management chronic pain in osteoarthritis, rheumatoid arthritis and pain due to other diseases and causes.

Most of the NSAIDs are administered orally. However, parenteral drug formulations have become very important particularly for drugs having analgesic, anti-inflammatory or antipyretic effects. Parenteral routes of administration, including subcutaneous, intramuscular, intrathecal, epidural and intravenous injection, offer numerous benefits over oral delivery. For example, parenteral administration of a drug typically results in attainment of a therapeutically effective blood concentration of the drug in a shorter time than is achievable by oral administration. This is especially true for intravenous injection, whereby the drug is placed directly into the bloodstream. Parenteral administration can also result in more predictable blood serum concentrations of a drug, because drug loss in the gastrointestinal tract due to absorption, distribution, metabolism, binding to food, and other causes is eliminated. Parenteral administration is the preferred method of drug delivery in emergency situations, and is also useful in treating subjects who are uncooperative, unconscious, or otherwise unable or unwilling to accept oral medication.

Acute pain is managed with a variety of drugs including opioid analgesics, e.g., morphine, hydromorphone, hydrocodone, oxycodone, tramadol, and codeine; acetaminophen; nonsteroidal anti-inflammatory drugs (NSAIDs) e.g., ketoprofen, ibuprofen, naproxen, tiaprofenic acid, aceclofenac, diclofenac, piroxicam, loxaprofen, fenoprofen, flurbiprofen, tenoxicam, lornoxicam, acetylsalicylic acid, flufenamic acid, mefenamic acid, nifluniic acid, tolfenamic acid, diflunisal, etodolac, fenbufen, isoxicam, pirprofen, sulindac, tolmetin, and piketoprofen and cyclo-oxygenase isoform 2 (COX-2) selective NSAIDs, e.g., celecoxib, valdecoxib, piketoprofen, etoricoxib, rofecoxib, and lumiracoxib.

Celecoxib is approved in U.S. under brand name CELEBREX® capsules and used in the treatment of osteoarthritis, rheumatoid arthritis, juvenile rheumatoid arthritis, ankylosing spondylitis, acute pain, chronic pain, primary dysmenorrhea and familial adenomatous polyposis.

Celecoxib was described in U.S. Pat. No. 5,466,823 assigned to Searle, a class of 1, 5-diaryl pyrazoles and their salts together with processes for the preparation of such compounds.

Celecoxib is chemically designated as 4-[5-(4-methylphenyl)-3-(trifluoromethyl)-1H-pyrazol-1-yl] benzenesulfonamide and is a diaryl-substituted pyrazole. The empirical formula is $C_{17}H_{14}F_3N_3O_2S$, and the molecular weight is 381.38; the chemical structure is as follows:

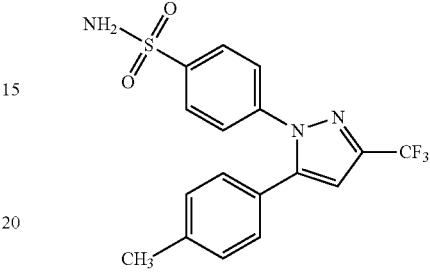

Celecoxib is a hydrophobic and highly permeable drug belonging to class II of biopharmaceutics classification system. Celecoxib is a neutral molecule that is essentially insoluble in water which leads to high variability in absorption and hence has dissolution rate limited bioavailability after oral administration. It also has pre-systemic metabolism. Peak plasma levels of celecoxib occurs approximately 3 hrs after an oral dose.

In acute pain, as in the case of surgical pain, trauma, pain due to kidney stones, and arthritis, which demands immediate relief parenteral route (injection, IV, etc.) is more efficient and prompt, as compared to the oral route.

The process of developing stable parenteral dosage forms for selective COX-2 inhibitors is challenging because of, amongst other things, low physical stability. Attempts have been made to formulate parenteral dosage forms for COX-2 inhibitors as lyophilized powders for reconstitution.

U.S. Pat. No. 6,589,557, assigned to Acusphere describes porous matrices of celecoxib with an enhanced rate of dissolution. The porous matrix may be reconstituted with an aqueous medium and administered parenterally.

U.S. Pat. No. 7,695,736 relates to parenterally deliverable formulations of water-soluble selective COX-2 inhibitory drugs and salts and prodrugs thereof. The invention describes dosage forms that are prepared as lyophilized powders for reconstitution.

U.S. Pat. No. 6,589,973 describes a clear stable pharmaceutical preparation of selective COX-2 inhibitors preferably in the parenteral form. It discloses that injectable formulations of COX-2 inhibitors can be obtained only when dissolved in a selective isosorbide type solvent.

U.S. Pat. Nos. 6,451,339 and 6,383,471 disclose compositions and methods for improved delivery of hydrophobic agents.

U. S. Application No. 2005/0191343 discloses reverse micellar formulations for the delivery of hydrophobic or lipophilic compounds, particularly therapeutic compounds.

PCT Publication WO 2008/077823 discloses self-microemulsifying drug delivery systems and microemulsions used to enhance the solubility of pharmaceutical ingredients comprising a polyoxyethylene sorbitan fatty acid ester emulsifier; a fatty acid ester co-emulsifier and oil.

U.S. Pat. No. 5,496,818 discloses a stable emulsion of the oil-in-water type with a phospholipid as emulsifier and the disperse phase have a positive zeta potential of at least +15, but preferably +30, mV after dilution of the emulsion ready for administration.

U.S. Pat. No. 6,007,826 discloses a cationic oil-in-water emulsion which comprises colloid particles in which a part of the surface-active agents or lipids in the interfacial film have positively charged polar groups, therefore the colloid particles having a positive zeta potential.

U.S. Pat. No. 8,298,568 discloses oil-in-water emulsion useful as a delivery vehicle of hydrophobic ingredients such as pharmaceutical drugs, wherein the emulsion particles have a net positive charge and comprises 0.001 to 0.1% of a cationic agent, 0 to 1% of a non-ionic emulsifier and 0 to 0.5% of an anionic emulsifier.

PCT Publication WO 2008/113177 discloses various compounds and compositions comprising polyunsaturated fatty acid monoglycerides and derivatives thereof.

There remains a long felt need to develop a parenteral composition for NSAID, especially for celecoxib that can be quite useful in acute conditions, such as post-operative pain, acute lower back pain, opioid-resistant pain, visceral pain, surgical pain, bone injury pain, pain during labor, pain resulting from burns, including sunburn, post-partum pain, genitourinary tract related pain including cystitis, and the nociceptive pain or nociception, and the like.

The present application relates to a parenteral composition for celecoxib or its pharmaceutically acceptable salts thereof, in the nanoemulsion form.

BRIEF SUMMARY OF THE INVENTION

In one aspect, the invention includes oil-in-water emulsion of celecoxib for parenteral administration, comprising: celecoxib, a discontinuous phase comprising an oil, a lecithin and an aqueous continuous phase; wherein the celecoxib is dissolved in the emulsion and being present in an amount of about 0.6% w/w of the emulsion, or less; and the weight ratio of celecoxib to lecithin is being about 0.1:1 or less, and wherein the emulsion is filterable through a 0.2 micron filter.

In some embodiments of this aspect, the total amount of oil is about 6% w/w of the emulsion or less, the combined amount of oil and lecithin is about 12% w/w of the emulsion, or less, and the emulsion has a viscosity of from about 1 cps to about 1000 cps, and is injectable.

These emulsions can have pH ranges from about 4 to about 9 and may optionally further comprise a chelating agent and a tonicity agent. The emulsions may also have an average droplet size of the discontinuous phase is about 200 nanometers or less.

Another aspect of the invention includes treating patients in pain. These methods of treating pain comprise parenterally administering to a patient in need thereof an amount of an emulsified celecoxib composition comprising celecoxib, a discontinuous phase comprising an oil, a lecithin, and an aqueous continuous phase; the celecoxib being present in an amount of about 0.6% w/w of the emulsion, or less; the weight ratio of celecoxib to lecithin being about 0.1:1 or less, the total amount of oil being about 6% w/w or less, the combined amount of oil and lecithin being about 12% w/w or less and the emulsion having a viscosity of about from about 1 cps to about 1000 cps, a pH ranging from about 4 to about 9 and being filterable through a 0.2 micron filter.

In these methods, the amount of celecoxib administered in a single parenteral dose ranges from about 50 mg to about 800 mg, and in some embodiments, from about 50 mg to about 200 mg.

Administration is generally preferred over a period of 15 mins to 45 mins.

Another way of describing methods of reducing pain in a human subject in need thereof in accordance with another aspect of the invention comprises administering to the patient at least one parenteral dose of an oil-in-water nanoemulsion composition comprising celecoxib at a concentration from about 0.5 mg/mL to about 20 mg/mL and in an amount of from about 50 mg to about 800 mg, wherein the mean droplet diameter of the nanoemulsion is about 200 nanometers or less, over a time period of from about 15 minutes to about 45 minutes.

In yet another aspect of the invention, there is provided a method of obtaining at least one of the following pharmacokinetic parameters: a mean peak plasma concentration ($C_{max}$) from about 750 ng/ml to about 20,300 ng/ml; an $AUC_{(0-12)}$ from about 1400 hr*ng/mL to about 55,300 hr*ng/mL; a $AUC_{last}$ from about 1300 hr*ng/mL to about 55,300 hr*ng/mL; or an $AUC_{(0-inf)}$ from about 14000 hr*ng/mL to about 55,300 hr*ng/mL; a total apparent volume of distribution ($V_{ss}$) from about 100 L to about 180 L; or a total apparent volume of distribution ($V_{ss}$) of said administration of nanoemulsion composition is less than 50 percent compared to total apparent volume of distribution ($V_{ss}$) of CELEBREX® 200 MG or CELEBREX® 400 MG. This is accomplished by administering to the patient at least one parenteral dose of an oil-in-water nanoemulsion composition comprising celecoxib at a concentration from about 0.5 mg/mL to about 20 mg/mL and in an amount of from about 50 mg to about 800 mg, over a time period of from about 15 minutes to about 45 minutes.

In still another aspect, there is provided a celecoxib nanoemulsion composition for parenteral administration to a human patient comprising: celecoxib in an amount of from about 0.005 to about 1.0% w/w of the composition, the discontinuous phase, the discontinuous phase accounting for about 5% to about 50% w/w of the composition; a continuous aqueous phase in an amount of from about 50% w/w to about 95% w/w of the composition; and an emulsifier in an amount of from about 0.01% to about 20% w/w of the composition, wherein the discontinuous phase has a mean droplet diameter of less than 200 nm.

In some embodiments of this aspect, in the celecoxib nanoemulsion compositions, the weight ratio of discontinuous non-aqueous phase to celecoxib is from about 100:1.0 to about 5.0:1.0 and/or the weight ratio of emulsifier to celecoxib is from about 1.0:1.0 to about 100.0:1.0 and/or the weight ratio of emulsifier to discontinuous non-aqueous phase is from about 1:10 to about 10:1.

The resulting celecoxib nanoemulsions sometimes desirably have at least one of the following characteristics: a PFAT value of less than 0.05%; a viscosity from about 1 cps to about 1000 cps; a pH value of from about 3 to about 9; a polydispersity index of about less than 0.8; a transmittance of greater than about 10%; a zeta potential in a range of −50 mV to +50 mV; a D50 of mean droplet diameter of less than 200 nm when measured at 2-8 degrees C.; 25 degrees C./60% RH and 30 degrees C. at 6 months; or both a D50 and D90 mean droplet diameter of less than 250 nm when measured 30 degrees C. at 6 months.

There is also provided, in another aspect, a method of making a nanoemulsion composition of celecoxib for parenteral administration comprising: providing celecoxib, an emulsifier, an oil, and water; wherein the amount of emulsifier is equal to or greater than the amount of oil, the amount of water is from about 85 to about 95% w/w, and the amount of celecoxib is from about 0.005 to about 0.5% w/w; and microfluidizing at a pH ranging from about 7.5 to about 9.0 and a pressure of from about 10,000 to about 30,000 psi thereby forming an nanoemulsion wherein the mean droplet diameter is less than about 200 nm. This method can further include forming a coarse emulsion before microfluidizing wherein the coarse emulsion has a mean droplet diameter of greater than 200 nm to about 800 nm and wherein coarse emulsion formation occurs at a pH that is higher than the pH used for microfluidizing.

In yet another aspect, the invention is a method of reducing pain in a human subject in need thereof comprising a single parenteral administration of nanoemulsion composition comprising celecoxib in an amount of from about 50 mg to about 800 mg, wherein the nanoemulsion composition is administered over a time period of from about 15 minutes to about 45 minutes. The nanoemulsion composition used can include celecoxib in a concentration of about 0.6% of the emulsion, or less. The nanoemulsion composition used can include celecoxib in a concentration from about 0.5 mg/mL to about 20 mg/mL. In one embodiment, the administration of this nanoemulsion composition over this period of about 15 to about 45 minutes provides a mean peak plasma concentration ($C_{max}$) of at least about 3 times that resulting from the oral administration of an equivalent (e.g., about 200 mg IV vs. about 200 mg orally) amount of celecoxib. In another embodiment, the mean peak plasma concentration ($C_{max}$) is at least about 4 times that resulting from the oral administration of an equivalent amount of celecoxib and in a further embodiment, the $C_{max}$ is at least about 5 times greater.

In addition, in some embodiments, these methods of treatment just described, using the celecoxib nanoemulsions of the invention, provides at least one of following pharmacokinetic parameters: a mean peak plasma concentration ($C_{max}$) from about 750 ng/ml to about 5200 ng/ml; a mean peak plasma concentration ($C_{max}$) for a 50 mg infusion of from about 750 ng/ml to about 1000 ng/ml; a mean peak plasma concentration ($C_{max}$) for a 100 mg infusion of from about 1700 ng/ml to about 2000 ng/ml; a mean peak plasma concentration ($C_{max}$) for a 200 mg infusion of from about 3900 ng/ml to about 5000 ng/ml; an $AUC_{(0-12)}$ of from about 1400 hr*ng/mL to about 8500 hr*ng/mL; an $AUC_{(0-12)}$ for a 50 mg infusion of from about 1400 hr*ng/mL to about 1700 hr*ng/mL; an $AUC_{(0-12)}$ for a 100 mg infusion of from about 3000 hr*ng/mL to about 4500 hr*ng/mL; an $AUC_{(0-12)}$ for a 200 mg infusion of from about 7000 hr*ng/mL to about 8500 hr*ng/mL; an $AUC_{last}$ from about 1300 hr*ng/mL to about 9500 hr*ng/mL; an $AUC_{last}$ for a 50 mg infusion of from about 1500 hr*ng/mL to about 1750 hr*ng/mL; an $AUC_{last}$ for a 100 mg infusion of from about 3800 hr*ng/mL to about 4800 hr*ng/mL; an $AUC_{last}$ for a 200 mg infusion of from about 7500 hr*ng/mL to about 9500 hr*ng/mL; an $AUC_{(0-inf)}$ from about 1400 hr*ng/mL to about 10000 hr*ng/mL; an $AUC_{(0-inf)}$ for a 50 mg infusion of from about 1550 hr*ng/mL to about 1950 hr*ng/mL; an $AUC_{(0-inf)}$ for a 100 mg infusion of from about 3800 hr*ng/mL to about 4800 hr*ng/mL; and an $AUC_{(0-inf)}$ for a 200 mg infusion of from about 7500 hr*ng/mL to about 9500 hr*ng/mL.

In another aspect, the invention is a celecoxib containing emulsion composition comprising: celecoxib, a lecithin, an oil, and water, wherein celecoxib concentration in the formulation is no more than about 0.6% by weight of the emulsion, the celecoxib to lecithin weight ratio is no greater than about 0.1:1, and the emulsion is filterable through a 0.2 micrometer membrane. Another aspect of the invention is the parenteral administration of these formulations to a patient in need of pain treatment.

In still another embodiment of this aspect, the total oil content of the emulsion is no more than about 6% by weight and the combined concentration of the oil and lecithin in the oil phase is no more than about 12% by w/w of the formulation. Desirably, the emulsion is not viscous and is injectable by a syringe or needle. The pH of the emulsion is desirably between about 4 and about 9. Another aspect of the invention is the parenteral administration of these formulations to a patient in need of pain treatment.

In an embodiment, the concentration of celecoxib in the emulsion is 0.6% w/w or less. In another embodiment, the viscosity of the emulsion is 1000 cps or less. In a further embodiment, the emulsion is injectable and is desirably between a pH of about 4 and about 9. In still a further embodiment, the concentration of celecoxib ranges from about 0.1 to about 0.3 percent and in particular is about 0.2 percent.

The emulsions described above can also include conventional additives such as EDTA, sucrose, glycerin, and histidine.

The invention also relates to methods of using the celecoxib formulations to treat pain. The invention is a method of reducing pain in a human subject in need thereof comprising a single parenteral administration of nanoemulsion composition comprising celecoxib in an amount of from about 50 mg to about 800 mg, wherein the nanoemulsion composition is administered over a time period of from about 15 minutes to about 45 minutes. The nanoemulsion composition used can include celecoxib in a concentration from about 0.5 mg/mL to about 20 mg/mL. Moreover, this method results in a total apparent volume of distribution (Vss) of administration of celecoxib containing nanoemulsion composition is less than 50 percent compared to total apparent volume of distribution (Vss) of CELEBREX® 200 MG or CELEBREX® 400 MG. Indeed, in some embodiments, the administration of nanoemulsion composition of the invention in accordance with these methods provides a total apparent volume of distribution (Vss) from about 100 L to about 180 L.

In another aspect, the invention is a method of reducing pain in a human subject in need thereof comprising a single parenteral administration of nanoemulsion composition comprising celecoxib in an amount of from about 50 mg to about 800 mg, wherein the nanoemulsion composition is administered over a time period of from about 15 minutes to about 45 minutes. The nanoemulsion composition used can include celecoxib in a concentration from about 0.5 mg/mL to about 20 mg/mL. The method results in a 90% Confidence Interval (CI) of the relative mean $AUC_{(0-inf)}$ and/or $AUC_{(0-t)}$ is within 80.00% to 125.00% of $AUC_{(0-inf)}$ and/or $AUC_{(0-t)}$ of CELEBREX® 400 mg oral capsule when administered in the fasting state.

Another aspect of the invention is a method of reducing pain, such as acute pain in a human subject in need thereof comprising an initial parenteral administration of a nanoemulsion composition comprising celecoxib in amount of from about 50 mg to about 800 mg followed by a plurality of additional parenteral administrations of a nanoemulsion composition comprising celecoxib in amount of from about 50 mg to about 800 mg thereafter as determined by attending physician. These additional parenteral administrations can occur at an interval of every 2 hours (q2), every 4 hours (q4), every 6 hours (q6), every 8 hours (q8), every 10 hours (q10) or every 12 hours (q12), and the interval can vary between successive doses. The parenteral administrations are each administered over a time period of from about 15 minutes to about 45 minutes.

In some instances, these methods result in at least one of following pharmacokinetic parameters: a mean peak plasma concentration ($C_{max}$) from about 750 ng/ml to about 20,300 ng/ml; an $AUC_{(0-12)}$ from about 1400 hr*ng/mL to about 55,300 hr*ng/mL; a $AUC_{last}$ from about 1300 hr*ng/mL to about 55,300 hr*ng/mL; or an $AUC_{(0-inf)}$ from about 14000 hr*ng/mL to about 55,300 hr*ng/mL; a total apparent volume of distribution ($V_{ss}$) from about 100 L to about 180 L; or a total apparent volume of distribution ($V_{ss}$) of said administration of nanoemulsion composition is less than 50 percent compared to total apparent volume of distribution ($V_{ss}$) of CELEBREX® 200 MG or CELEBREX® 400 MG.

In another aspect, the invention provides a method of administering a single or multiple parenteral dose of a nanoemulsion composition of celecoxib, each dose containing an amount of from about 50 mg to about 800 mg, wherein the amount, frequency and number of doses is determined by the attending medical professional by reviewing various vital signs of human subjects in need thereof. These vital signs include (without limitation):

a. Gastrointestinal (GI) observations for GI tract ulcerations and bleeding;

b. Hepatic (Liver) function tests for liver enzymes like Aspartate aminotransferase (AST or S-GOT), Alanine Aminotransferase (ALT or S-GPT) and hepatic injury;

c. Blood pressure fluctuations or hypertension or new onset or worsening of hypertension;

d. Fluid retention and edema;

e. Congestive heart failure and Edema and cardiovascular thrombotic events;

f. Renal function test such as for serum creatinine, blood urea nitrogen and tests for renal papillary necrosis and other renal injury.

DETAILED DESCRIPTION

The term "comprising" (and its grammatical variations) as used herein is meant to be open ended and used in the inclusive sense of "having" or "including" and not in the exclusive sense of "consisting only of." The term "consisting essentially of", as used herein means the claimed elements and others, but is meant to exclude things that are inconsistent with the basic and novel characteristics of the inventions The terms "a" and the as used herein are understood to encompass the plural as well as the singular or otherwise clearly mentioned wherever needed. For example, reference to "an excipient" includes reference to one or more of such excipients, and reference to "the carrier" includes reference to one or more of such carriers.

The terms such as 'about', 'up to', 'generally', 'substantially' and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value. The term "about" is used to provide flexibility to a numerical range endpoint by providing that a given value may be "a little above" or "a little below" the endpoint. As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum.

As used herein, "free of" or "substantially free of" a particular compound or compositions or excipients refer to the absence of any separately added portion of the referenced compound or composition or excipients.

As used herein, an "effective amount" or a "therapeutically effective amount" of a drug refers to a non-toxic, but sufficient amount of the drug, to achieve therapeutic results in treating a condition for which the drug is known to be effective. In this instance, an effective amount is an amount of celecoxib which is sufficient to treat pain in a patient in need thereof which is to say to provide some measure of analgesia to reduce at least the patient's perception of pain.

The term "celecoxib" as used herein includes celecoxib or its pharmaceutically acceptable salts which are, within the scope of sound medical judgment, suitable for use in humans and lower animals without undue toxicity, irritation, allergic response and the like, which are well known in the art. The salts can be prepared in situ during the final isolation and purification of the compounds of the invention, or separately by reacting the pharmaceutically active substance, having a freebase function, with a suitable organic acid or inorganic acid. The term "celecoxib" is also meant to embrace any polymorph, pseudo-polymorph, solvate, hydrate, crystalline or amorphous form of celecoxib and any prodrug of celecoxib which can be delivered in a vehicle and manner described herein for celecoxib.

As used herein the term "pain" shall refer to all types of pain such as acute pain, post-operative pain, acute lower back pain, opioid-resistant pain, chronic pain such as chronic lower back pain; visceral pain, breakthrough pain, surgical pain, bone injury pain, pain during labor and delivery, pain resulting from burns, including sunburn, postpartum pain, and genitourinary tract related pain including cystitis, the term shall also refer to nociceptive pain or nociception.

As used herein, the terms "composition" and "formulation" are used interchangeably and refer to a mixture of two or more compounds, elements, or molecules. Also the terms "formulation" and "composition" may be used to refer to a mixture of one or more active agents with a carrier or other excipients. Furthermore, the term "dosage form" can include one or more formulation(s) or composition(s) provided in a format for administration to a subject.

As used herein, the term "mammal" shall refer to the Mammalia class of higher vertebrates. The term "mammal" includes, but is not limited to, a human.

The terms "emulsion" and "oil-in-water emulsion" as used herein, and unless otherwise stated or understood from the context used, refers to a colloidal dispersion system in which liquid oil is dispersed as droplets (the discrete phase, also referred to as "the discontinuous non-aqueous phase") in an continuous aqueous medium (the continuous phase, also referred to as "the continuous aqueous phase"). In some embodiments, at least 80% of the celecoxib w/w is dissolved and remains in the emulsion. In certain embodiments, greater than 85%, 90%, 95% or 99% of the drug is present in the discontinuous phase.

The term "nanoemulsion" as used herein, refers to an emulsion wherein the particle size diameter of the spherical domains or droplets of the discontinuous oil phase is less than 2000 nm. In certain embodiments, the particle size diameter is less than 1000 nm or 800 nm or 600 nm or 400 nm or 200 nm.

The term "oil" as used herein, means a general sense to identify hydrocarbon derivatives, carbohydrate derivatives, or similar organic compounds that are liquid at body temperatures, e.g., about 37° C. and are pharmacologically acceptable in injectable compositions. It includes glycerides or non-glycerides. These are generally non-polar compounds that are not immediately miscible with water.

The term "oil component" and "non-aqueous phase" are used interchangeably and refers to oil, or a combination of multiple oils and oil soluble pharmaceutically acceptable excipients.

As used herein, the term "medium chain fatty acid" means a saturated or unsaturated fatty acid having a carbon chain length of 6 to 12 carbon atoms, whereas the term "long chain fatty acid" means a saturated or unsaturated fatty acid having a carbon chain length of greater than 12 carbon atoms.

As used herein, the term "$AUC_{(last)}$" means the area under the plasma concentration versus time curve, from time 0 to the last measurable concentration as calculated by the linear trapezoidal method.

As used herein, the term "$AUC_{(0-12)}$" means the area under the plasma concentration versus time curve, from time 0 to the 12-hour time point, as calculated by the linear trapezoidal method.

As used herein, the term "$AUC_{(0-inf)}$" means the area under the plasma concentration versus time curve from time 0 to infinity. $AUC_{(0-inf)}$ is calculated as the sum of $AUC_{(last)}$ plus the ratio of the last measurable plasma concentration to the elimination rate constant.

As used herein, the term "Total apparent volume of distribution ($V_{ss}$)" means total apparent volume of distribution following single IV dose administration calculated as $$V_{ss} = MRT_{0-inf} \times CL.$$

In one embodiment, the present application relates to a method of reducing pain in a human subject in need thereof comprising a parenteral administration of nanoemulsion composition comprising celecoxib in an amount of from about 50 mg to about 800 mg, wherein the nanoemulsion composition is administered over a time period of from about 15 minutes to about 45 minutes.

In another embodiment, the method of reducing pain in a human subject in need thereof comprises of administering nanoemulsion composition comprising of celecoxib in an amount of from about 50 mg to about 800 mg, or from about 50 mg to about 600 mg or from about 50 mg to about 400 mg or from about 50 mg to about 200 mg or from about 50 mg to about 100 mg. In yet another aspect the nanoemulsion composition comprises of 50 mg or 100 mg or 200 mg or 600 mg or 800 mg of celecoxib.

In another embodiment, the method of reducing pain in a human subject in need thereof comprises of administering nanoemulsion composition comprising celecoxib in a concentration from about 0.5 mg/mL to about 20 mg/mL. In another aspect, the nanoemulsion composition comprises of celecoxib in a concentration from about 0.5 mg/mL to about 10 mg/mL. In yet another aspect, the nanoemulsion composition comprises of 1 mg/ml or 2 mg/ml of celecoxib.

In another embodiment, the method of reducing pain in a human subject in need thereof comprises of administering nanoemulsion composition via various parenteral routes, such as intravenous bolus, intramuscular, intra-articular, intra-peritoneal, intravenous infusion or any other suitable parenteral route.

In another embodiment, the method of reducing pain in a human subject in need thereof comprises of administering nanoemulsion composition over a time period of from about 15 minutes to about 45 minutes or over a time period of from about 15 minutes to about 35 minutes or over a time period of from about 15 minutes to about 25 minutes or over a period of about 15 minutes.

In some embodiments, the method of reducing pain in a human subject in need thereof comprises of administering nanoemulsion composition as a single parenteral administration of nanoemulsion composition comprising celecoxib in an amount of from about 50 mg to about 800 mg or as a multiple parenteral administration of nanoemulsion composition comprising celecoxib in an amount of from about 50 mg to about 800 mg.

In another embodiment, the method of reducing pain in a human subject in need thereof comprises of a single parenteral administration of nanoemulsion composition comprising celecoxib in an amount of from about 50 mg to about 800 mg followed by multiple parenteral administration of nanoemulsion composition comprising celecoxib in an amount of from about 50 mg to about 800 mg. In yet another aspect the multiple parenteral administration of nanoemulsion composition comprising celecoxib in an amount of from about 50 mg to about 800 mg after the first single parenteral administration of nanoemulsion composition as determined by the attending physician.

In some embodiment, the method of reducing acute pain in a human subject in need thereof comprising a single parenteral administration of nanoemulsion composition comprising celecoxib in amount of from about 50 mg to about 800 mg followed by multiple parenteral administration of nanoemulsion composition comprising celecoxib in amount of from about 50 mg to about 800 mg thereafter as determined by attending physician. In another embodiment, the multiple parenteral administration of nanoemulsion composition comprising celecoxib is administered at an interval of every 2 hours (q2), every 4 hours (q4), every 6 hours (q6), every 8 hours (q8), every 10 hours (q10) or every 12 hours (q12). In yet another aspect, the multiple parenteral administration of nanoemulsion composition comprising celecoxib is administered at an interval as determined by the attending physician.

In still other embodiments, the invention is treating pain in a patient in need thereof by administering to that patient an amount of a celecoxib-containing emulsion sufficient to treat and/or at least mitigate the patient's pain. This is accomplished by administering one or more parenteral doses of a celecoxib-containing emulsion comprising celecoxib, a lecithin, an oil, and water, wherein celecoxib in the formulation is no more than about 0.6% by weight of the emulsion, and the celecoxib to lecithin weight ratio is no greater than about 0.1:1. In some particular embodiments of this method, the formulations used are further characterized by one or more of the following: the total oil content of the emulsion is no more than about 1% by weight of the emulsion; and/or the combined concentration of the oil and lecithin in the oil phase is no more than about 12% by weight of the emulsion. Desirably the emulsion is at least one of: injectable through a syringe; has a viscosity of about 1,000 cps or less; has a pH of about 4 to about 9; and/or has a mean droplet size of the discontinuous phase of about 200 nanometers or less; and/or is filterable through a 0.2 micrometer filter on membrane. The emulsion is generally administered over a period of less than about an hour and more often about 15 to about 45 minutes.

An emulsion is considered injectable if the force required to expel the emulsion through a needle is no more than 160 mPa. Above 160 mPa, it becomes uncomfortable to inject the emulsion manually. For a given emulsion, its injection force is directly proportional to its viscosity. When using a regular syringe (e.g. 6.35 mm plunger diameter), a needle (e.g. 21-28 G) and at the normal injection rate (3-6 mL/min), a viscosity of no more than about 1000 cps is generally desired in order to be able to withdraw the emulsion into the syringe from a vial and then inject comfortably.

In the development of the emulsion of the current invention, it was noticed that more celecoxib can be dissolved if the oil and lecithin concentration is increased, however, with the increase in oil and/or lecithin concentration, the viscosity of the emulsion is increased making it difficult inject through the needle. The compositions of the current invention achieves a balance between desired celecoxib solubility (e.g. up to 0.6% w/w) and viscosity (no more than 1000 cps).

In some embodiments, the oil phase comprises medium chain triglyceride ("MCT") which can be use either alone or in combination with one or more vegetable oils. MCTs may also be used with other mono, di, and tri glycerides such as long chain triglycerides or "LCTs". Indeed, LCTs can also be used instead of MCTs. Any injectable vegetable oil such as soybean oil, corn oil, safflower oil, sesame oil, olive oil, castor oil of a mixture thereof may be used for the oil phase and a lecithin is any lecithin such as soy lecithin and egg lecithin or mixture thereof.

Celecoxib is associated with an increased risk of serious cardiovascular thrombotic events, myocardial infarction, and stroke. This risk may increase with duration of use and with higher dosage. Patients with cardiovascular disease or risk factors for cardiovascular disease may be at greater risk. Celecoxib is also been reported to be associated with increased gastrointestinal risk. Celecoxib causes an increased risk of serious gastrointestinal adverse events including bleeding, ulceration, and perforation of the stomach or intestines, which can be fatal. These events can occur at any time during use and without warning symptoms. Elderly patients are at greater risk for serious gastrointestinal (GI) events. To ensure safety and provide maximum benefit of parenteral administration of celecoxib in human subjects, it is necessary to monitor various vital signs and various organ functions like hepatic functions, renal and cardiovascular functions. The attending physician can monitor the patient's organ functions and other vital signs which would serve as a guide to administer proper dose, frequency and interval of multiple dosing of parenteral celecoxib to provide effective analgesia or effective reduction of pain in human subjects, in need thereof.

In some embodiment, single or multiple parenteral administration of nanoemulsion composition of celecoxib in amount of from about 50 mg to about 800 mg is administered as determined by the attending physician based on the effective analgesia or effective reduction of pain in human subjects, in need thereof.

In some embodiment, single or multiple parenteral administration of nanoemulsion composition of celecoxib in amount of from about 50 mg to about 800 mg is administered, as determined by the attending physician by reviewing various vital signs and laboratory evaluation reports of human subjects in need thereof.

The vital signs or periodic laboratory evaluations comprises:

a. Gastrointestinal (GI) observations for GI tract ulcerations and bleeding;
b. Hepatic (Liver) function tests for liver enzymes like Aspartate aminotransferase (AST or S-GOT), Alanine Aminotransferase (ALT or S-GPT) and hepatic injury;
c. Blood pressure fluctuations or hypertension or new onset or worsening of hypertension;
d. Fluid retention and edema;
e. Congestive heart failure and Edema and cardiovascular thrombotic events;
f. Renal function test such as for serum creatinine, blood urea nitrogen and tests for renal papillary necrosis and other renal injury, etc.

In some embodiment, multiple parenteral administration of nanoemulsion composition of celecoxib in amount of from about 50 mg to about 800 mg is determined by physician by performing following steps:

a. conducting periodic laboratory evaluations;
b. reviewing patients periodic laboratory evaluations;
c. determining the duration of treatment needed; and
d. determining the amount and interval of multiple administration of celecoxib required for effective analgesia or effective reduction in pain in human subject in need thereof.

In one embodiment, the present application relates to a method of reducing pain in a human subject in need thereof comprising a parenteral administration of any nanoemulsion composition described herein comprising celecoxib, wherein the nanoemulsion composition is administered over a time period of from about 15 minutes to about 45 minutes provides a mean peak plasma concentration ($C_{max}$) of at least about 3 times to that of the $C_{max}$ resulting from the equivalent amount of oral administration of celecoxib, and in another embodiment, at least about 4 times that of the $C_{max}$ of oral administration. In still another embodiment, the result is a $C_{max}$ that is at least 5 times that of oral administration.

In another embodiment, the present application relates to a method of reducing pain in a human subject in need thereof comprising a parenteral administration of nanoemulsion composition comprising celecoxib in an amount of from about 50 mg to about 800 mg, wherein the nanoemulsion composition is administered over a time period of from about 15 minutes to about 45 minutes provides mean peak plasma concentration ($C_{max}$) of from about 750 ng/ml to about 22,000 ng/ml.

In another embodiment, the present application relates to a method of reducing pain in a human subject in need thereof comprising multiple parenteral administration of nanoemulsion composition comprising celecoxib in an amount of from about 50 mg to about 800 mg, wherein the nanoemulsion composition is administered over a time period of from about 15 minutes to about 45 minutes provides mean peak plasma concentration ($C_{max}$) of from about 750 ng/ml to about 22,000 ng/ml.

In another embodiment, the present application relates to a method of reducing pain in a human subject in need thereof comprising a single parenteral administration of nanoemulsion composition comprising celecoxib in an amount of from about 50 mg to about 800 mg followed by multiple parenteral administration of nanoemulsion composition comprising celecoxib in an amount of from about 50 mg to about 800 mg wherein the nanoemulsion composition is administered over a time period of from about 15 minutes to about 45 minutes provides mean peak plasma concentration ($C_{max}$) of from about 750 ng/ml to about 22,000 ng/ml.

In some embodiments, single parenteral administration of nanoemulsion composition comprising celecoxib in an amount of from about 50 mg to about 800 mg provides mean peak plasma concentration ($C_{max}$) of from about 750 ng/ml to about 22,000 ng/ml.

In another aspect, single parenteral administration of nanoemulsion composition comprising celecoxib in an amount of from about 50 mg to about 200 mg provides mean peak plasma concentration ($C_{max}$) of from about 750 ng/ml to about 5,200 ng/ml. In yet another aspect, single parenteral administration of nanoemulsion composition comprising of 50 mg celecoxib provides mean peak plasma concentration ($C_{max}$) of from about 750 ng/ml to about 1000 ng/ml. In yet another aspect, single parenteral administration of nanoemulsion composition comprising of 100 mg celecoxib provides mean peak plasma concentration ($C_{max}$) of from about 1700 ng/ml to about 2000 ng/ml. In yet another aspect, single parenteral administration of nanoemulsion composition comprising of 200 mg celecoxib provides mean peak plasma concentration ($C_{max}$) of from about 3900 ng/ml to about 5200 ng/ml.

In one embodiment, the present application relates to a method of reducing pain in a human subject in need thereof comprising a parenteral administration of nanoemulsion composition comprising celecoxib in an amount of from about 50 mg to about 800 mg, wherein the nanoemulsion composition is administered over a time period of from about 15 minutes to about 45 minutes provides AUC of from about 1300 hr*ng/mL to about 54,000 hr*ng/mL.

In one embodiment, the present application relates to a method of reducing pain in a human subject in need thereof comprising multiple parenteral administration of nanoemulsion composition comprising celecoxib in an amount of from about 50 mg to about 800 mg, wherein the nanoemulsion composition is administered over a time period of from about 15 minutes to about 45 minutes provides AUC of from about 1300 hr*ng/mL to about 54,000 hr*ng/mL.

In one embodiment, the present application relates to a method of reducing pain in a human subject in need thereof comprising a single parenteral administration of nanoemulsion composition comprising celecoxib in an amount of from about 50 mg to about 800 mg followed by multiple parenteral administration of nanoemulsion composition comprising celecoxib in an amount of from about 50 mg to about 800 mg wherein the nanoemulsion composition is administered over a time period of from about 15 minutes to about 45 minutes provides AUC of from about 1300 hr*ng/mL to about 54,000 hr*ng/mL.

In some embodiments, single parenteral administration of nanoemulsion composition comprising celecoxib in an amount of from about 50 mg to about 800 mg provides AUC of from about 1300 hr*ng/mL to about 30,000 hr*ng/mL.

In another aspect, single parenteral administration of nanoemulsion composition comprising celecoxib in an amount of from about 50 mg to about 800 mg provides $AUC_{(0-inf)}$ of from about 1300 hr*ng/mL to about 30,000 hr*ng/mL. In yet another aspect, single parenteral administration of nanoemulsion composition comprising of 50 mg celecoxib provides $AUC_{(0-inf)}$ of from about 1550 hr*ng/mL to about 1950 hr*ng/mL. In yet another aspect, single parenteral administration of nanoemulsion composition comprising of 100 mg celecoxib provides $AUC_{(0-inf)}$ of from about 3800 hr*ng/mL to about 4,800 hr*ng/mL. In yet another aspect, single parenteral administration of nanoemulsion composition comprising of 200 mg celecoxib provides $AUC_{(0-inf)}$ of from about 7500 hr*ng/mL to about 9500 hr*ng/mL.

In another aspect, single parenteral administration of nanoemulsion composition comprising celecoxib in an amount of from about 50 mg to about 800 mg provides $AUC_{(0-12)}$ of from about 1300 hr*ng/mL to about 30,000 hr*ng/mL. In yet another aspect, single parenteral administration of nanoemulsion composition comprising of 50 mg celecoxib provides $AUC_{(0-12)}$ of from about 1400 hr*ng/mL to about 1700 hr*ng/mL. In yet another aspect, single parenteral administration of nanoemulsion composition comprising of 100 mg celecoxib provides $AUC_{(0-12)}$ of from about 3000 hr*ng/mL to about 4,500 hr*ng/mL. In yet another aspect, single parenteral administration of nanoemulsion composition comprising of 200 mg celecoxib provides $AUC_{(0-inf)}$ of from about 7000 hr*ng/mL to about 8500 hr*ng/mL.

In another aspect, single parenteral administration of nanoemulsion composition comprising celecoxib in an amount of from about 50 mg to about 800 mg provides $AUC_{(last)}$ of from about 1300 hr*ng/mL to about 30,000 hr*ng/mL. In yet another aspect, single parenteral administration of nanoemulsion composition comprising of 50 mg celecoxib provides $AUC_{(last)}$ of from about 1500 hr*ng/mL to about 1750 hr*ng/mL. In yet another aspect, single parenteral administration of nanoemulsion composition comprising of 100 mg celecoxib provides $AUC_{(last)}$ of from about 3800 hr*ng/mL to about 4,800 hr*ng/mL. In yet another aspect, single parenteral administration of nanoemulsion composition comprising of 200 mg celecoxib provides $AUC_{(last)}$ of from about 7500 hr*ng/mL to about 9500 hr*ng/mL.

In one embodiment, the method of reducing pain in a human subject in need thereof comprising a parenteral administration of nanoemulsion composition comprising celecoxib in an amount of from about 50 mg to about 800 mg, wherein the nanoemulsion composition is administered over a time period of from about 15 minutes to about 45 minutes provides total apparent volume of distribution ($V_{ss}$) of less than about 50 percent compared to total apparent volume of distribution ($V_{ss}$) of CELEBREX® 200 MG or CELEBREX® 400 MG.

In another embodiment, the method of reducing pain in a human subject in need thereof comprising a single parenteral administration of nanoemulsion composition comprising celecoxib in an amount of from about 50 mg to about 800 mg, wherein the nanoemulsion composition is administered over a time period of from about 15 minutes to about 45 minutes provides total apparent volume of distribution ($V_{ss}$) of less than about 50 percent compared to total apparent volume of distribution ($V_{ss}$) of CELEBREX® 200 MG or CELEBREX® 400 MG.

In another embodiment, the method of reducing pain in a human subject in need thereof comprising a multiple parenteral administration of nanoemulsion composition comprising celecoxib in an amount of from about 50 mg to about 800 mg, wherein the nanoemulsion composition is administered over a time period of from about 15 minutes to about 45 minutes provides total apparent volume of distribution ($V_{ss}$) of less than about 50 percent compared to total apparent volume of distribution ($V_{ss}$) of CELEBREX® 200 MG or CELEBREX® 400 MG.

In another embodiment, the method of reducing pain in a human subject in need thereof comprising a single parenteral administration of nanoemulsion composition comprising celecoxib in an amount of from about 50 mg to about 800 mg followed by multiple parenteral administration of nanoemulsion composition comprising celecoxib in an amount of from about 50 mg to about 800 mg wherein the nanoemulsion composition is administered over a time period of from about 15 minutes to about 45 minutes provides total apparent volume of distribution ($V_{ss}$) of less than about 50 percent compared to total apparent volume of distribution ($V_{ss}$) of CELEBREX® 200 MG or CELEBREX® 400 MG.

In another aspect, the method of reducing pain in a human subject in need thereof comprising a parenteral administration of nanoemulsion composition comprising celecoxib in an amount of from about 50 mg to about 800 mg, wherein the nanoemulsion composition is administered over a time period of from about 15 minutes to about 45 minutes provides total apparent volume of distribution ($V_{ss}$) of from about 100 L to about 180 L.

In yet another aspect, the method of reducing pain in a human subject in need thereof comprises of single or multiple parenteral administration of nanoemulsion composition comprising celecoxib in an amount of from about 50 mg to about 800 mg provides total apparent volume of distribution ($V_{ss}$) of from about 100 L to about 180 L.

In yet another aspect, the method of reducing pain in a human subject in need thereof comprises of a single parenteral administration of nanoemulsion composition comprising celecoxib in an amount of from about 50 mg to about 800 mg followed by multiple parenteral administration of nanoemulsion composition comprising celecoxib in an amount of from about 50 mg to about 800 mg provides total apparent volume of distribution ($V_{ss}$) of from about 100 L to about 180 L.

In one embodiment, the method of reducing pain in a human subject in need thereof comprising a parenteral administration of nanoemulsion composition comprising celecoxib in an amount of from about 50 mg to about 800 mg, wherein the nanoemulsion composition is administered over a time period of from about 15 minutes to about 45 minutes provides 90% Confidence Interval (CI) of the relative mean $AUC_{(0-inf)}$ and/or $AUC_{(0-t)}$ is within 80.00% to 125.00% of $AUC_{(0-inf)}$ and/or $AUC_{(0-t)}$ of CELEBREX® oral capsule when administered in the fed state.

In another embodiment, the method of reducing pain in a human subject in need thereof comprising a single parenteral administration of nanoemulsion composition comprising celecoxib in an amount of from about 50 mg to about 200 mg, wherein the nanoemulsion composition is administered over a time period of from about 15 minutes to about 45 minutes provides 90% Confidence Interval (CI) of the relative mean $AUC_{(0-inf)}$ and/or $AUC_{(0-t)}$ is within 80.00% to 125.00% of $AUC_{(0-inf)}$ and/or $AUC_{(0-t)}$ of CELEBREX® 400 mg oral capsule when administered in the fed state.

In another embodiment, the method of reducing pain in a human subject in need thereof comprising a single parenteral administration of nanoemulsion composition comprising celecoxib in an amount of from about 50 mg to about 200 mg, wherein the nanoemulsion composition is administered over a time period of from about 15 minutes to about 45 minutes provides 90% Confidence Interval (CI) of the relative mean $AUC_{(0-inf)}$ and/or $AUC_{(0-t)}$ is within 80.00% to 125.00% of $AUC_{(0-inf)}$ and/or $AUC_{(0-t)}$ of CELEBREX® 200 mg oral capsule when administered in the fed state.

In another embodiment, the method of reducing pain in a human subject in need thereof comprising a single parenteral administration of nanoemulsion composition comprising celecoxib in an amount of from about 50 mg to about 100 mg, wherein the nanoemulsion composition is administered over a time period of from about 15 minutes to about 45 minutes provides 90% Confidence Interval (CI) of the relative mean $AUC_{(0-inf)}$ and/or $AUC_{(0-t)}$ is within 80.00% to 125.00% of $AUC_{(0-inf)}$ and/or $AUC_{(0-t)}$ of CELEBREX® 100 mg oral capsule when administered in the fed state.

In one embodiment, the present application relates to parenteral nanoemulsion composition comprising therapeutically effective amount of celecoxib. In another embodiment, the present application relates to parenteral nanoemulsion composition comprising therapeutically effective amount of celecoxib, a discontinuous non-aqueous phase, a continuous aqueous phase, and other pharmaceutically acceptable excipients.

In yet another embodiment, the present application relates to parenteral nanoemulsion composition comprising therapeutically effective amount of celecoxib, at least one oil, a continuous aqueous phase, and other pharmaceutically acceptable excipients.

In another embodiment, the nanoemulsion composition of celecoxib for parenteral administration in the form of oil-in-water emulsion, comprising: celecoxib in an amount of from about 0.005 to about 1.0% w/w of the composition, a discontinuous non-aqueous phase in an amount of from about 05% w/w to about 50% w/w of the composition, a continuous aqueous phase in an amount of from about 50% w/w to about 95% w/w of the composition, and an emulsifier in an amount of from about 0.01% to about 20% w/w of the composition, wherein the nanoemulsion has a mean droplet diameter of less than 200 nm.

In another embodiment, discontinuous non-aqueous phase comprises of oil and/or oil soluble active or other oil soluble pharmaceutically acceptable excipients or mixtures or combinations thereof.

In another embodiment, continuous aqueous phase comprises emulsifiers and/or water soluble active and/or other water soluble pharmaceutically acceptable excipients or mixtures or combinations thereof.

In another embodiment, nanoemulsion composition of present application comprises emulsifiers and/or co-emulsifiers which include, but not limited to, emulsifiers of natural or synthetic origins or mixtures thereof.

In another embodiment, nanoemulsion composition of present application comprises emulsifiers and/or co-emulsifiers which include, but not limited to, nonionic, anionic, cationic or zwitterionic surfactants and phospholipids or mixtures thereof.

In another embodiment, nanoemulsion composition of present application is substantially free of toxic solubilizers for parenteral compositions like polyoxyethylene sorbitan fatty acid esters (e.g., TWEENS), polyoxyethylene castor oil derivatives (e.g., CREMOPHOR), and poloxamer (e.g., PLURONIC), bile salt, cyclodextrins and mixtures thereof.

In another embodiment, nanoemulsion composition of present application comprises emulsifiers such as phospholipids which include, but not limited to, pure phosphatidyl choline or mixtures of phospholipids, which include phosphatidyl choline, phosphatidyl serine, phosphatidyl ethanolamine, phosphatidyl inositol, other phospholipids, diglycerides of fatty acids linked to an ester of phosphoric acid.

In another embodiment, phospholipids include, but are not limited to, soy lecithin, egg lecithin, hydrogenated soy lecithin, hydrogenated egg lecithin, sphingosine, gangliosides, and phytosphingosine and combinations thereof. Phospholipids can also be synthesized and the common synthetic phospholipids may include but are not limited to diacylglycerols, phosphatidic acids, phosphocholines, phosphoethanolamines, phosphoglycerols, phosphoserines, lysophospholipids, and pegylated phospholipids.

In certain embodiments, the oil component or discontinuous non aqueous phase of the present application comprises a monoglyceride, a diglyceride, a triglyceride, or a mixture thereof. In certain embodiments, the oil component comprises an ester formed between one or more fatty acids and an alcohol other than glycerol.

In another embodiment, nanoemulsion composition of present application comprises of oil which includes, but not limited to, any oil approved for human or animal consumption by the FDA including natural oils such as plant or animal oils or their derivatives or synthetic oils and especially natural oil. Examples of such oils include, essential oils, vegetable oils, hydrogenated vegetable oils, such as peanut oil, canola oil, avocado oil, safflower oil, olive oil, corn oil, soy bean oil, sesame oil, vitamin A, vitamin D, vitamin E, fish oils, monoglyceride, a diglyceride, a triglyceride or mixtures thereof.

In another embodiment, oil includes, but not limited to, medium chain fatty acids, long chain fatty acids or mixtures thereof.

In another embodiment, suitable medium chain fatty acids (MCFA) include, but are not limited to, both even and odd fatty acids, such as fatty acids containing C4 (butyric acid, butanoic acid), C5 (valeric acid), C6 (caproic acid, hexanoic acid), C7 (heptanoic acid), C8 (caprylic acid, octanoic acid), C9 (pelargonic acid), C10 (capric acid, decanoic acid), C11 (undecanoic acid) or C12 (lauric acid, dodecanoic acid). The MCFA may be monoglyceride, a diglyceride, a triglyceride, or a mixture thereof. Further the MCFA triglyceride component may be a naturally occurring triglycerides containing composition, such as butterfat and coconut oil. Alternatively, said triglyceride component may comprise one or more industrially prepared triglycerides or a mixture of naturally occurring and industrially prepared triglycerides. Said triglyceride may be prepared by interesterification of C4 to C12 chain fatty acids.

Suitable examples of long chain triglyceride-containing oils for use in the compositions of the present application include, but not limited to, almond oil; babassu oil; borage oil; black currant seed oil; canola oil; castor oil; coconut oil; corn oil; cottonseed oil; emu oil; evening primrose oil; flax seed oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; a mixture of hydrogenated cottonseed oil and hydrogenated castor oil; partially hydrogenated soybean oil; a mixture of partially hydrogenated soybean oil and partially hydrogenated cottonseed oil; glyceryl trioleate; glyceryl trilinoleate; glyceryl trilinolenate; a omega-3 polyunsaturated fatty acid triglyceride containing oil; and or mixtures thereof. In another embodiment, nanoemulsion composition of present application comprises discontinuous non-aqueous phase comprising of at least one oil in an amount of from about 0.01% to about 20% by weight, from about 0.5% to about 10% by weight, or from about 1% to about 5% by weight, based on the total weight of the composition.

In another embodiment, nanoemulsion composition of present application comprises of at least one emulsifier and/or co-emulsifier in an amount of from about 0.01% to about 20% by weight, from about 0.5% to about 10% by weight, or from about 1% to about 5% by weight, based on the total weight of the composition.

In another embodiment, nanoemulsion composition of present application comprises of celecoxib in an amount of from about 0.01% to about 3% by weight, from about 0.1% to about 2% by weight, or from about 0.1% to about 0.5% by weight, based on the total weight of the composition.

In another embodiment, nanoemulsion composition of present application comprises of at least one chelating agent is in an amount of from about 0.001% to about 2% by weight, from about 0.001% to about 0.01% by weight, or from about 0.002% to about 0.01% by weight, based on the total weight of the composition.

In another embodiment, nanoemulsion composition of present application comprises of at least one sugar and/or sugar alcohol is in an amount of from about 0.01% to about 20% by weight, from about 0.5% to about 10% by weight, or from about 1% to about 5% by weight, based on the total weight of the composition.

In another embodiment, nanoemulsion composition of present application comprises a discontinuous non-aqueous phase and celecoxib in a weight ratio of from about 100:1 to about 5:1.

In another embodiment, nanoemulsion composition of present application comprises at least one emulsifier and celecoxib in a weight ratio of from about 1:1 to about 100:1.

In another embodiment, nanoemulsion composition of present application comprises at least one emulsifier and at least one oil in a weight ratio of from about 1:10 to about 10:1.

In another embodiment, nanoemulsion composition of present application comprises at a sugar and/or sugar alcohol in an amount of from about 1% to about 10% by weight, from about 1% to about 10% by weight, or from about 1% to about 5% by weight, based on the total weight of the composition.

Nanoemulsions are highly unstable and require proper formulation to ensure its stability. To ensure the stability of nanoemulsion various parameters need to be studied. A key for preparing a stable nanoemulsion requires right value of zeta potential and polydispersity index.

Zeta potential is a key factor that is important in emulsion stability. Zeta potential is a measure of the electrical charge stabilization of an emulsion system and will depend on the composition of dispersion medium. Zeta potential is an important tool for understanding and predicting the long term stability of the emulsion. The zeta potential is a measure of the magnitude of the repulsion or attraction between particles. Zeta potential analysis is a technique for determining the surface charge of nanoparticles in solution. Nanoparticles have a surface charge that attracts a thin layer of ions of opposite charge to the nanoparticle surface. This double layer of ions travels with the nanoparticle as it diffuses throughout the solution. The electric potential at the boundary of the double layer is known as the Zeta potential of the particles and has values that typically range from +100 mV to −100 mV. The magnitude of the zeta potential is predictive of the colloidal stability. Nanoemulsions or nanoparticles with zeta potential in a range of −50 mV to +50 mV such as −10 mV, −20 mV, −30 mV, 0 mV, +10 mV, +20 mV, +30 mV and the like typically have high degrees of stability. Polydispersity index (PDI) is another important parameter, which is a measure of the width of the particle size distribution. Polydispersity indices less than 0.5 are typically referred to as "monodisperse." A PDI value of 1 indicates that the sample has a very broad size distribution and may contain large particles or aggregates that could be slowly sedimenting. Particle size, zeta potential and polydispersity index can be determined using various instruments. For example, particle size analyzer using laser light scattering such as Zetasizer™ apparatus available from Malvern Instruments Ltd.

In another embodiment, wherein the oil droplets of nanoemulsion of present application has mean particle diameter size range of about 5 nm to about 500 nm, from about 5 nm to about 500 nm, from about 5 nm to about 400 nm, from about 5 nm to about 300 nm, from about 5 nm to about 200 nm, from about 5 nm to about 100 nm, or less than about 100 nm.

The, D50 and D90 represent, the median or the $50^{th}$ percentile and the $90^{th}$ percentile of the particle size distribution, respectively, as measured by volume. This means, the term "D50" is defined as the size in microns below which 50 percent of the particles reside on a volume basis and similarly, the term "D90" is defined as the size in microns below which 90 percent of the particles reside, on a volume basis. Particle size can be determined, for example, by laser light scattering using a particle size analyzer, such as the proprietary Zetasizer™ apparatus available from Malvern Instruments Ltd.

In another embodiment, wherein the nanoemulsion, has D90 particle size of less than about 500 nm, D90 particle size of less than about 400 nm, D90 particle size of less than about 300 nm, D90 particle size of less than about 200 nm, D90 particle size of less than about 100 nm or D90 particle size of less than about 90 nm.

In another embodiment, wherein the nanoemulsion, has D50 particle size of less than about 500 nm, D50 particle size of less than about 400 nm, D50 particle size of less than about 300 nm, D50 particle size of less than about 200 nm, D50 particle size of less than about 100 nm or D50 particle size of less than about 90 nm.

In another embodiment, parenteral nanoemulsion composition of the present application has zeta potential in a range of −50 mV to +50 mV such as −10 mV, −20 mV, −30 mV, 0 mV, +10 mV, +20 mV or +30 mV.

In another embodiment, parenteral nanoemulsion composition of the present application comprises of celecoxib, a discontinuous non-aqueous phase, a continuous aqueous phase, and other pharmaceutically acceptable excipients, wherein said composition has a zeta potential in a range of −50 mV to +50 mV such as −10 mV, −20 mV, −30 mV, 0 mV, +10 mV, +20 mV or +30 mV and has a polydispersity index of about less than 1.0, of about less than 0.8, or of about less than 0.5, such as less than 0.4, less than 0.3, less than 0.2, or less than 0.1.

In another embodiment, parenteral nanoemulsion composition of the present application comprises celecoxib, at least one emulsifier, at least one oil and other pharmaceutically acceptable excipients, wherein said composition has a zeta potential in a range of −50 mV to +50 mV such as −10 mV, −20 mV, −30 mV, 0 mV, +10 mV, +20 mV, +30 mV etc.

In another embodiment, parenteral nanoemulsion composition of the present application has a polydispersity index of about less than 1.0, of about less than 0.8, or of about less than 0.5, such as less than 0.4, less than 0.3, less than 0.2, or less than 0.1.

In another embodiment, parenteral nanoemulsion composition of the present application comprises celecoxib, at least one emulsifier, at least one oil, and other pharmaceutically acceptable excipients, wherein said composition has a polydispersity index of about less than 1.0.

In another embodiment, parenteral nanoemulsion composition of the present application comprises celecoxib, at least one emulsifier, at least one oil and other pharmaceutically acceptable excipients, wherein said composition has a zeta potential in a range of −50 mV to +50 mV such as −10 mV, −20 mV, −31 mV, 0 mV, +10 mV, +20 mV, +30 mV and polydispersity index of about less than 1.0.

Transmittance is the fraction of incident light or any other electromagnetic radiation at a specified wavelength that passes through a sample. A spectrophotometer is employed to measure the amount of light that a sample absorbs or transmits.

In another embodiment, the nanoemulsion composition of present application is semitransparent or translucent, determined by the transmittance, measured at a wavelength of about from about 400 nm to about 800 nm using a quartz cuvette with 1 mm path length, and is greater than about 1% or greater than about than about 2%.

In another embodiment, the nanoemulsion composition of present application is semitransparent or translucent, determined by the transmittance, measured at a wavelength of about from about 400 nm to about 800 nm using a quartz cuvette with 1 mm path length, is from about 1% to about 99% such as 5%, 10%, 15% 20%, 25%, 30%, 35%, 40%, 45%, 50% 60%, 70%, 80% or 99%.

In another embodiment, the nanoemulsion composition of present application is semitransparent or translucent, determined by the transmittance, measured at a wavelength of about from about 400 nm to about 800 nm using a quartz cuvette with 1 mm path length, is from about 1% to about 99% such as from about 1% to about 10%, from about 5% to about 15%, from about 5% to about 20%, from about 5% to about 25%, from about 10% to about 30%, from about 15% to about 35%.

In another embodiment, the PFAT (%) value is from about 0 to about 0.1, such as from about 0.001% to about 0.05%, from about 0.001% to about 0.04%, from about 0.001% to about 0.02%, from about 0.001% to about 0.01%, from about 0.005% to about 0.05%, or from about 0.01% to about 0.05%. The PFAT (%) value is determined using the United States Pharmacopeia method under Chapter <729>, which measures volume percent of large droplets with diameter>5 micron or PFATS in parenteral emulsions. PFATS limit is being set at 0.05% by volume of the total oil phase and is considered to have greater implications for IV infusion safety. PFATS value is an indicator of presence of large particles including oil aggregates.

In another embodiment, nanoemulsion composition of present application further comprises common excipients that include, but are not limited to, buffers, cosolvents, water for injection, cryo-protectant, saline, glucose solutions, pH adjustment agents, antioxidants, chelating agents e.g. EDTA or histidine, acidifying, alkalizing, preservatives, a viscosity modifier, a pH adjusting agent osmolality or isotonicity agents and the like or mixtures or combinations thereof.

In another embodiment, the composition of present application has osmolality of from about 100 to about 500 mOsm.

In another embodiment, the pH of the composition of present application is generally from about 3 to about 10, from about 6 to about 8. In other embodiment, the pH of the composition is about 3, 4, 5, 6, 7, 8, or 9. In another embodiment the pH of the composition is from the following ranges: 3.0 to 6.0; 6.0 to 6.9; 6.0 to 7.0; 7.0 to 7.9; 7.0 to 8.0; 8.0 to 9.0; and 7.6 to 10.0.

In another embodiment, the nanoemulsion compositions of present application are stable over period of 1 month, 3 month 6 month and 12 month or more.

In yet another aspect, the nanoemulsion compositions of present application has following characteristics:

a. D50 of mean droplet diameter is less than 250 nm;
b. D50 and D90 mean droplet diameter are less than 250 nm.
  c. PFAT value of less than 0.05%;
  d. viscosity from about 1 cps to about 1000 cps;
  e. pH value of from about 3 to about 9;
  f. polydispersity index of about less than 0.8;
  g. transmittance of greater than about 10%; or
  h. zeta potential in a range of −50 mV to +50 mV.
    when measured at 2-8 degrees C., 25 degrees C./60% RH and 30 degrees C. at 6 months.

In another embodiment, the nanoemulsion composition of celecoxib for parenteral administration in the form of oil-in-water emulsion, comprising: celecoxib in an amount of from about 0.005 to about 1.0% w/w of the composition, a discontinuous non-aqueous phase in an amount of from about 05% w/w to about 50% w/w of the composition, a continuous aqueous phase in an amount of from about 50% w/w to about 95% w/w of the composition, and an emulsifier in an amount of from about 0.01% to about 20% w/w of the composition, wherein the nanoemulsion has a mean droplet diameter of less than 200 nm. In yet another aspect, the nanoemulsion composition provides $AUC_{(0-inf)}$ of at least about 1300 hr*ng/ml;

a total blood concentration of at least about 550 ng/mL at 15 mins after IV administration of the nanoemulsion composition;

a total blood descending blood concentration of at least 200 ng/mL celecoxib within about 60 minutes after IV administration of the nanoemulsion composition;

a $T_{max}$ of from about 8 and to about 25 minutes after IV administration of the nanoemulsion composition;

a $C_{max}$ of from about t8 and to about 25 minutes after IV administration of the nanoemulsion composition;

an onset of analgesia in from about 15 mins to about 3 hours a $T_{max}$ of between 10 and 20 minutes after IV administration; and a blood concentration of up to about 1,000 ng/mL at about 1 hour and up to about 200 ng/mL at about 2 hours after administration of a dose of celecoxib between about 25 and about 800 mg given over a period of no more than about 15 mins.

In another embodiment, osmolality, isotonicity or tonicity agents may include one or more tonicity agents, such as salts (e.g., as sodium chloride or potassium chloride) or sugars or sugar alcohol such as glycerol, mannitol, sorbitol, mannitol, dextrose, glycerin, sucrose, or trehalose, polyethylene glycol, propylene glycol, albumin, amino acid and mixtures thereof. The type and amount of tonicity agent can be selected by one of skill in the art using known techniques.

In another embodiment, the nanoemulsion may be administered to an animal in need thereof via various routes, such as intravenous, intramuscular, intra-articular, intra-peritoneal, or any other suitable parenterally route, or via topical application or oral administration.

In certain embodiments, the composition of the present application may be filter sterilized using via 0.2 μm filters.

The term "filter sterilized" means a composition that has passed through a filter having a pore size sufficiently small to result the composition free or substantially free of bacterial contaminants Bacteria generally range in size from about 0.2 μm to about 600 μm, with most bacteria having a size in the range of about 1 μm to about 10 μm. Filters or membranes having pore size of about 0.22 μm or less (0.2 μm) are considered to produce sterile filtrates and are sufficiently small to result in a filter sterilized composition.

Such filters and filter kits are available from Millipore Corporation, as well as other manufacturers.

In another embodiment, the composition of present application is directed to use in the treatment and/or prophylaxis of cyclooxygenase-2 mediated conditions and disorders in an animal need thereof.

In another embodiment, the composition of present application is used for treatment or prevention of pain such as acute pain, neuropathic pain, and post-operative pain, acute lower back pain, opioid-resistant pain, visceral pain, surgical pain, bone injury pain, pain during labor and delivery, pain resulting from burns, including sunburn, post-partum pain, and genitourinary tract-related pain including cystitis, the term shall also refer to nociceptive pain or nociception in patients need thereof.

In another embodiment, the composition of present application is ready to inject or intravenous infusion without any dilution or mixing with other liquid.

In another embodiment, the composition of present application is ready to inject or intravenous infusion along with 0.9% saline or isotonic dextrose or glucose solution or without any further dilution or mixing with other parenteral liquids.

In yet another embodiment, the present application relates to parenteral nanoemulsion composition comprising therapeutically effective amount of celecoxib or its pharmaceutically acceptable salt thereof, at least one oil, an continuous aqueous phase, and other pharmaceutically acceptable excipients, wherein said composition is essentially free of solid, crystalline or amorphous particles.

In another embodiment, the present application relates method of treatment or prevention of pain by administering to an animal in need thereof a parenteral nanoemulsion composition comprising therapeutically effective amount of celecoxib or its pharmaceutically acceptable salt celecoxib, at least one emulsifier and/or co-emulsifiers, at least one oil and other pharmaceutically acceptable excipients, wherein said composition has a zeta potential in a range of −50 mV to +50 mV, and polydispersity index of about less than 1.0, of about less than 0.8.

In another embodiment, the parenteral nanoemulsion composition described herein does not cause vein irritation.

In another embodiment, the nanoemulsion may be prepared in different ways known to ordinary person skilled in the art. Exemplary process comprises the preparation of the aqueous and non-aqueous phases separately. The aqueous phase contains all water soluble pharmaceutically acceptable excipients like emulsifiers, isotonizing agents, stabilizers, preservatives and buffer agents in the suitable proportion. The non-aqueous phase contains the active substance totally or partially solubilized in the oil and it may contain antioxidants, stabilizers or other oil soluble pharmaceutically acceptable excipients. For the preparation of the emulsion the non-aqueous phase is added to the aqueous phase under moderate agitation and subsequently the particle size is reduced by a homogenizer, until an average particle size smaller than 500 nm is obtained. Droplets of this size can also be obtained by using high pressure homogenizers or any other apparatus that allows the particle size to be adequately reduced.

The methods used to produce nanoemulsions can be divided into the high- and low-energy ones. High-energy methods include high-pressure homogenization and microfluidization which can be used at both laboratory and industrial scale as well as ultrasonification which is primarily used at laboratory scale. Other methods for preparing nanoemulsion include spontaneous emulsification, the solvent-diffusion method, solvent displacement phase inversion composition method and the phase-inversion temperature (PIT) method. A lipophilic drug can be added to the oil phase whereas a hydrophilic one can be solubilized in the aqueous phase.

In high-pressure homogenization, the coarse dispersion of the oil and aqueous phase is passed through a small inlet orifice at an operating pressure in the range of 500-100000 psi, where the emulsion mixture is subjected to intense turbulence and hydraulic shear which then produces a fine emulsion with an extremely small droplet size. Microfluidization uses a high pressure positive displacement pump operating at very high pressures, up to 20,000 psi, which forces the emulsion product through the interaction chamber which consists of a series of microchannels. The emulsion flows through the microchannels on to an impingement area resulting in very fine emulsion droplets. The operating pressure and the number of passes of the coarse emulsion through the interaction chamber of the microfluidizer determine the particle size of the fine emulsion. The higher the operating pressure and the number of passes, the smaller the droplet size of the final emulsion. The resulting nanoemulsion can then be filtered through a 0.2 μm filter to remove any large particles present resulting in a uniform nanoemulsion. High-energy emulsification methods can produce both o/w and w/o nanoemulsions.

Among the low-energy emulsification methods, solvent diffusion PIT generates o/w nanoemulsions, whereas spontaneous emulsification produces w/o nanoemulsion. In the PIT method, oil, water and nonionic surfactants are mixed together at room temperature. Mixture typically comprises o/w micro-emulsions coexisting with excess oil, and the surfactant monolayer exhibits positive curvature. When this macro-emulsion is heated gradually, the polyethoxylated surfactant becomes lipophilic and at higher temperatures, the surfactant gets completely solubilized in the non-aqueous phase and the initial o/w emulsion undergoes phase inversion to w/o emulsion. In the solvent displacement method non-aqueous phase is dissolved in water-miscible organic solvents, such as acetone, ethanol and ethyl methyl ketone. The organic phase is poured into an aqueous phase containing surfactant to yield spontaneous nanoemulsion by rapid diffusion of organic solvent. The organic solvent is removed from the nanoemulsion by a suitable means, such as vacuum evaporation. Spontaneous nanoemulsification has also been reported when solution of organic solvents containing a small percentage of oil is poured into aqueous phase without any surfactant.

In another embodiment, the nanoemulsion composition of celecoxib for parenteral administration as per present application is manufactured as follows:
  a. providing ingredients including an emulsifier, an oil, water and optionally a chelating agent, a tonicity agent, a pH adjusting agent, a preservative, a viscosity modifier, wherein the amount of emulsifier is equal to or greater than the amount of oil, and the amount of water is from about 85 to about 95% w/w, and the amount of celecoxib is from about 0.005 to about 0.5% w/w;
  b. microfluidizing the ingredients at a pH ranging from about 7.5 to about 9.0 and a pressure of from about 10,000 to about 30,000 psi; and
  c. forming an nanoemulsion wherein the mean droplet diameter is less than about 200 nm.

In another embodiment, microfluidization is carried out at a pH of from about 7.5 to about 8.5 and a pressure of from about 18,000 and about 30,000 psi. In another aspect, microfluidization is carried out at a pH of from about 7.5 to about 8.5 and a pressure of more than 20,000 psi.

In another embodiment, the nanoemulsion composition is manufactured by preparing a coarse emulsion before microfluidizing. The coarse emulsion is not formed by microfluidizing. The coarse emulsion has a mean particle diameter size of from about 300 to about 800 nm. The coarse emulsion is formed at a pH of about 7.9 or higher and microfluidizing occurs at a pH of about 7.9 or below or coarse emulsion is formed at a pH of about 8.0 to about 8.5 and microfluidizing occurs at a pH of about 7.5 to about 7.9.

In another embodiment, the nanoemulsion composition has D50 of mean droplet diameter of the discontinuous non-aqueous phase is less than 200 nm when measured as at 2-8 degrees C., 25 degrees C./60% RH and 30 degrees C. at 6 months following microfluidizing.

In another embodiment, the nanoemulsion composition has D50 and D90 of mean droplet diameter of the discontinuous non-aqueous phase are less than 250 nm when measured 30 degrees C. 6 months following microfluidizing.

In another embodiment, the nanoemulsion composition has mean particle size of mean droplet diameter of the discontinuous non-aqueous phase has a poly-dispersant index of 0.04 or above at 6 months when tested at 2-8 degrees C., 25 degrees C./60% RH and 30 degrees C. 6 months following microfluidizing.

In one embodiment, the present application relates to nanoemulsion composition comprising celecoxib in amount of from about 50 mg to about 800 mg, wherein the said nanoemulsion composition is packaged in suitable dosage units, such as for example ampoules, infusion bags, vials or bottles for treating or reducing pain in a human subject in need thereof.

In another embodiment, the present application relates to a kit for infusion or parenteral administration of nanoemulsion composition comprising celecoxib in amount of from about 50 mg to about 800 mg wherein the said nanoemulsion composition is packaged in suitable dosage units, such as for example ampoules, infusion bags, vials or bottles for reducing pain in a human subject in need thereof. In yet another embodiment, the dosage unit comprises of 25 ml of nanoemulsion composition containing 50 mg of celecoxib. In yet another embodiment, the dosage unit comprises of 50 ml of nanoemulsion composition containing 100 mg of celecoxib. In yet another embodiment, the dosage unit comprises of 100 ml of nanoemulsion composition containing 200 mg of celecoxib.

For example the kit comprises of dosage unit such as ampoules for infusion or parenteral administration for reducing pain in a human subject in need thereof, wherein the kit may comprises of ampoule containing 25 ml of nanoemulsion composition containing 50 mg of celecoxib, ampoule containing 50 ml of nanoemulsion composition containing 100 mg of celecoxib, ampoule containing 100 ml of nanoemulsion composition containing 200 mg of celecoxib.

In another embodiment, the present application relates to a kit for infusion or parenteral administration of nanoemulsion composition comprising celecoxib in amount of from about 50 mg to about 800 mg wherein the said nanoemulsion composition is packaged in prefilled syringes for reducing pain in a human subject in need thereof. In yet another embodiment, the prefilled syringe comprises of 25 ml of nanoemulsion composition containing 50 mg of celecoxib or of 50 ml of nanoemulsion composition containing 100 mg of celecoxib or of 100 ml of nanoemulsion composition containing 200 mg of celecoxib.

The present application is further illustrated by the examples which are provided merely to be exemplary of the nanoemulsion composition described above and do not limit the scope of the application. Certain modifications and equivalents will be apparent to those skilled in the art and are intended to be included within the scope of the present application.

In another aspect, the invention provides nanoemulsion compositions of celecoxib for parenteral administration, comprising: celecoxib in amount of from about 50 mg to about 800 mg; a discontinuous non-aqueous phase; a continuous aqueous phase wherein the nanoemulsion has a mean droplet diameter of less than 200 nm.

In still another aspect, the invention provides a nanoemulsion composition of celecoxib for parenteral administration in the form of oil-in-water emulsion, comprising: celecoxib in an amount of from about 0.005 to about 1.0% w/w of the composition, the discontinuous phase, the discontinuous phase accounting for about 5% to about 50% w/w of the composition; a continuous aqueous phase in an amount of from about 50% w/w to about 95% w/w of the composition; and an emulsifier in an amount of from about 0.01% to about 20% w/w of the composition, wherein the nanoemulsion, that is at least the discontinuous phase, has a mean droplet diameter of less than 200 nm. The emulsifier comprises soy lecithin, egg lecithin, hydrogenated soy lecithin, hydrogenated egg lecithin, soy phosphatidyl choline, egg phospholipid and/or combinations thereof. The discontinuous non-aqueous phase comprises an oil selected from a monoglyceride, a diglyceride, a triglyceride or mixture thereof.

In some embodiments of this aspect, the weight ratio of discontinuous non-aqueous phase to celecoxib is from about 100:1.0 to about 5.0:1.0 and/or the weight ratio of emulsifier to celecoxib is from about 1.0:1.0 to about 100.0:1.0 and/or the weight ratio of emulsifier to discontinuous non-aqueous phase is from about 1:10 to about 10:1. Moreover, in certain embodiments, these celecoxib nanoemulsion compositions have at least one of the following characteristics: a PFAT value of less than 0.05%; a viscosity from about 1 cps to about 3 cps; a pH value of from about 3 to about 9; a polydispersity index of about less than 0.8; a transmittance of greater than about 10%; a zeta potential in a range of −50 mV to +50 mV; a $D_{50}$ of mean droplet diameter of less than 200 nm when measured at 2-8 degrees C.; 25 degrees C./60% RH and 30 degrees C. at 6 months; or both a $D_{50}$ and $D_{90}$ mean droplet diameter of less than 250 nm when measured 30 degrees C. at 6 months.

In still another aspect, the compositions of the inventions described herein may be part of a kit comprising, for example, ampoules, vials, bottles, prefilled syringe or infusion bags containing 25 ml of a nanoemulsion composition containing 50 mg of celecoxib; containing 100 mg of celecoxib; or containing 200 mg of celecoxib.

Another aspect of the invention includes methods of making a nanoemulsion composition of celecoxib for parenteral administration comprising providing an emulsifier, an oil, water and optionally a chelating agent, a tonicity agent, a pH adjusting agent, a preservative, and/or a viscosity modifier, wherein the amount of emulsifier is equal to or greater than the amount of oil, and the amount of water is from about 85 to about 95% w/w, and the amount of celecoxib is from about 0.005 to about 0.5% w/w and microfluidizing the ingredients at a pH ranging from about 7.5 to about 9.0 and a pressure of from about 10,000 to about 30,000 psi thereby forming an nanoemulsion wherein the mean droplet diameter is less than about 200 nm. The range of pH and pressures used may also include microfluidization at a pH of from about 7.5 to about 8.5 and a pressure of from about 18,000 and about 30,000 psi and in another embodiment at a pH of from about 7.5 to about 8.5 and a pressure of more than 20,000 psi.

The method may also include the step of forming a coarse emulsion before microfluidizing wherein the coarse emulsion has a mean droplet diameter of greater than 200 nm such as from about 300 to about 800 nm Coarse emulsion formation can occurs at a pH of about 7.9 or higher while microfluidizing can occur at a pH of about 7.9 or below. In another embodiment, coarse emulsion formation occurs at a pH of about 8.0 to about 8.5 and microfluidizing occurs at a pH of about 7.5 to about 7.9. In some instances, the resulting microemulsion results in the $D_{50}$ of the mean droplet diameter of the discontinuous non-aqueous phase being less than 200 nm when measured as at 2-8 degrees C., 25 degrees C./60% RH and 30 degrees C. at 6 months following microfluidizing. Alternatively, both the $D_{50}$ and $D_{90}$ of mean droplet diameter of the discontinuous non-aqueous phase are less than 250 nm when measured 30 degrees C. 6 months following microfluidizing.

In still another aspect of the invention, there is provided a nanoemulsion composition of celecoxib for parenteral administration to human subject to treat pain which provides at least one of the following pharmacokinetic profile: an efficiency of at least about $AUC_{0-\infty}$ 1300 hr*ng/ml; a total blood concentration of at least about 550 ng/mL at 15 mins after IV administration of the celecoxib nanoemulsion; a total blood descending blood concentration of at least 200 ng/mL celecoxib within about 60 minutes after IV administration of the celecoxib nanoemulsion; a $t_{max}$ of between 10 and 20 minutes after IV administration of the celecoxib nanoemulsion; a $C_{max}$ of between 10 and 20 minutes after IV administration of the celecoxib nanoemulsion; an onset of analgesia in from about 15 mins to about 3 hours and a $t_{max}$ of between 10 and 20 minutes after IV administration; and/or a blood concentration of up to about 1,000 ng/mL at about 1 hour and up to about 200 ng/mL at about 2 hours after administration of a dose of celecoxib nanoemulsion between about 25 and about 800 mg given over a period of no more than about 15 mins.

EXAMPLES 1-11

The right combination of oil and emulsifier (lecithin) is selected based on their physical characteristics. The following examples exemplify various combinations to arrive stable emulsion.

| Ex. | Egg Lecithin (% w/w) | Soy Lecithin (% w/w) | Total Lecithin (% w/w) | Soybean Oil (% w/w) | MCT Oil (% w/w) | Total Oil (% w/w) |
|---|---|---|---|---|---|---|
| Ex. 1 | 2 | 0 | 2 | 0 | 1 | 1 |
| Ex. 2 | 2 | 0 | 2 | 0 | 2 | 2 |
| Ex. 3 | 0 | 2 | 2 | 1 | 0 | 1 |
| Ex. 4 | 3 | 0 | 3 | 2.5 | 0 | 2.5 |
| Ex. 5 | 4 | 0 | 4 | 0 | 2 | 2 |
| Ex. 6 | 4 | 0 | 4 | 0 | 4 | 4 |
| Ex. 7 | 6 | 0 | 6 | 0 | 3 | 3 |
| Ex. 8 | 6 | 0 | 6 | 0 | 6 | 6 |
| Ex. 9 | 8 | 0 | 8 | 0 | 8 | 8 |

-continued

| Ex. | Egg Lecithin (% w/w) | Soy Lecithin (% w/w) | Total Lecithin (% w/w) | Soybean Oil (% w/w) | MCT Oil (% w/w) | Total Oil (% w/w) |
|---|---|---|---|---|---|---|
| Ex. 10 | 10 | 0 | 10 | 0 | 10 | 10 |
| Ex. 11 | 12 | 0 | 12 | 0 | 12 | 12 |

Procedure:

These formulations were made by the following general procedure:
1. Weigh out celecoxib ("CXB"), lecithin, oil, all other components and water
2. Mix well. Adjust pH
3. Apply homogenization by a high speed homogenizer (e.g. BeadBeater) or a high pressure homogenizer (e.g. microfluidizer)
4. Pass through a 0.2- or 0.45-micron filter
5. Determine CXB concentration in the filtrate by HPLC
6. Record appearance of the filtrate (emulsion)

| Ex. | Total Oil Phase (Lecithin + Oil % w/w) | Aqueous Phase** (% w/w) | CXB Solubility (% w/w) | CXB:Lecithin Weight Ratio (w/w) | Physical appearance | Suitable for Injection |
|---|---|---|---|---|---|---|
| Ex. 1 | 3 | 96.9 | 0.12 | 0.06 | Translucent, not viscous | Yes, preferred |
| Ex. 2 | 4 | 95.9 | 0.13 | 0.07 | Translucent, not viscous | Yes, preferred |
| Ex. 3 | 3 | 96.8 | 0.2 | 0.10 | Translucent, not viscous | Yes, preferred |
| Ex. 4 | 5.5 | 94.3 | 0.2 | 0.07 | Translucent, not viscous | Yes, preferred |
| Ex. 5 | 6 | 93.8 | 0.22 | 0.06 | Translucent, not viscous | Yes, preferred |
| Ex. 6 | 8 | 91.8 | 0.25 | 0.06 | Opaque, slightly viscous | Yes |
| Ex. 7 | 9 | 90.6 | 0.37 | 0.06 | Opaque, slightly viscous | Yes |
| Ex. 8 | 12 | 87.6 | 0.37 | 0.06 | Creamy, very viscous* | Too viscous to inject |
| Ex. 9 | 16 | 83.5 | 0.48 | 0.06 | Creamy, very viscous* | Too viscous to inject |
| Ex. 10 | 20 | 79.5 | 0.54 | 0.05 | Creamy, very viscous* | Too viscous to inject |
| Ex. 11 | 24 | 75.4 | 0.6 | 0.05 | Creamy, very viscous* | Too viscous to inject |

*Too viscous to withdraw by a syringe and a 21G needle or to filter
**Aqueous Phase contains 9% w/v sucrose, 0.0055% w/v EDTA disodium dihydrate and water at pH 7

EXAMPLES 12-20

The compositions are tabulated in table below:

| Composition (% w/w) | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|
| Celecoxib | 0.2 | 0.2 | 0.2 | 0.2 | 0.2 | 0.2 | 0.2 | 0.2 | 0.2 |
| Soy phosphatidylcholine | 2 | 3 | 4 | | | | | | |
| Soy lecithin | | | | 2 | 3 | 4 | | | |
| Egg lecithin | | | | | | | 3 | 3 | 4 |
| Soybean oil | 2.5 | 3 | 5 | 2.5 | 3 | 5 | 2.5 | 3 | 5 |
| Edetate disodium, dihydrate | 0.0055 | 0.0055 | 0.0055 | 0.0055 | 0.0055 | 0.0055 | 0.0055 | 0.0055 | 0.0055 |
| Glycerin | 2.25 | 2.25 | 2.25 | 2.25 | 2.25 | 2.25 | 2.25 | 2.25 | 2.25 |
| HCl/NaOH | pH adjustment | pH adjustment | pH adjustment | pH adjustment | pH adjustment | pH adjustment | pH adjustment | pH adjustment | pH adjustment |
| DI Water, (q.s.) | 100 | 100 | 100 | 100 | 100 | 100 | 100 | 100 | 100 |
| pH | 6-7 | 6-7 | 6-7 | 6-7 | 6-7 | 6-7 | 6-7 | 6-7 | 6-7 |

Procedure:
1. Celecoxib was mixed with all excipients and agitated by high shear mixer until a uniform emulsion was formed.
2. pH adjustment was made if required.
3. The crude emulsion was homogenized by microfluidiser (M110EH) to obtain a nanoemulsion in desired droplet size range.
4. The obtained nanoemulsion was passed through a 0.22 μfilter.

EXAMPLES 21-28

The parenteral nanoemulsion compositions comprising celecoxib or its pharmaceutically acceptable salt thereof may be prepared as given in the table below and using the process described in examples 12-20.

| Composition (% w/w) | Ex. 21 | Ex. 22 | Ex. 23 | Ex. 24 | Ex. 25 | Ex. 26 | Ex. 27 | Ex. 28 |
|---|---|---|---|---|---|---|---|---|
| Celecoxib | 0.2 | 0.2 | 0.2 | 0.2 | 0.2 | 0.2 | 0.2 | 0.2 |
| Soy phosphatidylcholine | 2 | 4 | 2 | 3 | 3 | 3 | 4 | 2 |
| Soybean oil | 1 | 5 | 5 | 3 | — | 1.5 | 5 | 1 |
| Medium chain triglycerides | — | — | — | — | 3 | 1.5 | — | — |
| Propylene glycol | 4 | 4 | 4 | 4 | 4 | 4 | 4 | 4 |
| Edetate disodium, dihydrate | 0.005 | 0.005 | 0.005 | 0.005 | 0.005 | 0.005 | 0.005 | 0.005 |
| Glycerin | 2.25 | 2.25 | 2.25 | 2.25 | 2.25 | 2.25 | 2.25 | 2.25 |
| HCl/NaOH | pH adjustment | pH adjustment | pH adjustment | pH adjustment | pH adjustment | pH adjustment | pH adjustment | pH adjustment |
| DI Water, (q.s.) | 100 | 100 | 100 | 100 | 100 | 100 | 100 | 100 |
| pH | 5 | 5 | 5 | 7 | 7 | 7 | 9 | 9 |

EXAMPLES 29-38

The parenteral nanoemulsion compositions comprising celecoxib or its pharmaceutically acceptable salt thereof may be prepared as given in the table below and using the process described in examples 12-20.

EXAMPLE 39

The parenteral nanoemulsion composition comprising celecoxib or its pharmaceutically acceptable salt thereof may be prepared as given in the table below and using the process described in examples 12-20.

| Composition (% w/w) | Ex 39 |
|---|---|
| Celecoxib | 0.2 |
| Egg phospholipid | 3 |
| Soybean oil | 2.5 |
| Edetate Disodium Dihydrate | 0.0055 |
| Glycerin | 2.25 |
| NaOH/HCl | pH Adjustment |
| DI water (q.s.) | 100 |
| pH | 8.0 |

EXAMPLE 40

A single-center study in 26 healthy subjects to assess pharmacokinetics of celecoxib nanoemulsion of Example 39 was performed. The objective of this study was to characterize the PK profile of single infusion of 50 mg, 100 mg and 200 mg doses of celecoxib nanoemulsion in comparison with the PK profile of oral Celebrex® 400 MG, in fed conditions. The results are tabulated in Table 1.

| Composition (% w/w) | Ex. 29 | Ex. 30 | Ex. 31 | Ex. 32 | Ex. 33 | Ex. 34 | Ex. 35 | Ex. 36 | Ex. 37 | Ex. 38 |
|---|---|---|---|---|---|---|---|---|---|---|
| Celecoxib | 0.2 | 0.2 | 0.2 | 0.2 | 0.2 | 0.2 | 0.2 | 0.2 | 0.2 | 0.2 |
| Egg phospholipid | 3 | 3 | 3 | 3 | 3 | 3 | 3 | 3 | 3 | 3 |
| Soybean oil | 2.5 | 2.5 | 2.5 | 2.5 | 2.5 | 2.5 | 2.5 | 2.5 | 2.5 | 2.5 |
| Edetate Disodium, dihydrate | 0.0055 | 0.0055 | 0.0055 | 0.0055 | 0.0055 | 0.0055 | 0.0055 | 0.0055 | 0.0055 | 0.0055 |
| Glycerin | 2.25 | 2.25 | 2.25 | 2.25 | 2.25 | 2.25 | 2.25 | 0 | 2.25 | 0 |
| Sucrose | | | | | | | | 10 | 0 | 10 |
| Histidine | | | | | | | | 0 | 0.085 | 0.085 |
| NaOH/HCl | pH adjustment | pH adjustment | pH adjustment | pH adjustment | pH adjustment | pH adjustment | pH adjustment | pH adjustment | pH adjustment | pH adjustment |
| DI water (q.s.) | 100 | 100 | 100 | 100 | 100 | 100 | 100 | 100 | 100 | 100 |
| pH | 4 | 5 | 6 | 7 | 7.5 | 8 | 9 | 7 | 7 | 7 |

TABLE 1

| | $AUC_{0-12}$ (hr * ng/ml) | $AUC_{last}$ (hr * ng/ml) | $AUC_{0-inf}$ (hr * ng/ml) | $V_{ss}$ (L) | $C_{max}$ (ng/ml) | $T_{max}$ (hr) |
|---|---|---|---|---|---|---|
| 400 mg Oral | | 14910 | 15215 | 352.5 | 1964 | 3.143 |
| 50 mg IV | 1540 | 1632.3 | 1767.9 | 138 | 863.6 | .25 |
| 100 mg IV | 3480 | 4102.9 | 4258.6 | 143 | 1837 | 0.2917 |
| 200 mg IV | 7327.4 | 8658.6 | 8980.3 | 145.9 | 4093 | 0.25 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

The invention claimed is:

1. An oil-in-water emulsion of celecoxib for parenteral administration, comprising: about 50 mg to about 800 mg of celecoxib, a discontinuous phase comprising an oil, a lecithin, and an aqueous continuous phase; wherein the celecoxib is present in an amount of about 0.6% w/w of the emulsion or less; and a weight ratio of the celecoxib to the lecithin is about 0.1:1 or less; and wherein the emulsion upon administration provides at least one of the following pharmacokinetic parameters following parenterally administering over a period of about 15 minutes to about to 45 minutes to a patient: a mean peak plasma concentration ($C_{max}$) from about 750 ng/ml to about 20,300 ng/ml; an $AUC_{(0-12)}$ from about 1400 hr*ng/mL to about 55,300 hr*ng/mL; a $AUC_{last}$ from about 1300 hr*ng/mL to about 55,300 hr*ng/mL; an $AUC_{(0-inf)}$ from about 14000 hr*ng/mL to about 55,300 hr*ng/mL; or a total apparent volume of distribution ($V_{ss}$) from about 100 L to about 180 L.

2. The emulsion of claim 1, wherein the emulsion comprises at least one of: a total amount of the oil is about 6% w/w of the emulsion or less; a combined amount of the oil and the lecithin is about 12% w/w of the emulsion or less; the emulsion has a viscosity of about from about 1 cps to about 1000 cps; or the emulsion is filterable through a 0.2 micron filter.

3. The emulsion of claim 1, wherein the emulsion has a pH value range from about 4 to about 9.

4. The emulsion of claim 1, wherein the discontinuous phase comprises a medium chain triglyceride, vegetable oil or a mixture thereof.

5. The emulsion of claim 1, wherein the lecithin is selected from soy lecithin, egg lecithin or mixture thereof.

6. The emulsion of claim 1, further comprising: a chelating agent, selected from EDTA or histidine.

7. The emulsion of claim 1, further comprising: a tonicity agent, selected from sucrose or glycerin.

8. The emulsion of claim 1, wherein an average droplet size of the discontinuous phase is about 200 nanometers or less.

9. The emulsion of claim 1, wherein the discontinuous phase is in an amount of from about 5% to about 50% w/w of the emulsion; the aqueous continuous phase is in an amount of from about 50% w/w to about 95% w/w of the emulsion; and the lecithin is in an amount of from about 0.01% to about 20% w/w of the emulsion, and the discontinuous phase has a mean droplet diameter of less than 200 nm.

10. The emulsion of claim 9, wherein the emulsion has at least one of the following characteristics: a PFAT value of less than 0.05%; a viscosity from about 1 cps to about 3 cps; a pH value of from about 3 to about 9; a polydispersity index of about less than 0.8; a transmittance of greater than about 10%; a zeta potential in a range of −50 mV to +50 mV; a D50 of mean droplet diameter of less than 200nm when measured at 2-8 degrees C.; 25 degrees C./60% RH and 30 degrees C. at 6 months; or both a D50 and D90 mean droplet diameter of less than 250 nm when measured 30 degrees C. at 6 months.

11. An injectable oil-in-water emulsion of celecoxib comprising: celecoxib at a concentration of from about 0.005 to about 1.0% w/w of the emulsion and in an amount of from about 50 mg to about 800 mg; a discontinuous phase comprising an oil which is a medium chain triglyceride, vegetable oil or a mixture thereof, in an amount of from about 5% to about 50% w/w of the emulsion; a lecithin in an amount of from about 0.01% to about 20% w/w of the emulsion; an aqueous continuous phase in an amount of from about 50% w/w to about 95% w/w of the emulsion, wherein a weight ratio of the celecoxib to the lecithin is about 0.1:1 or less;

wherein the emulsion upon administration provides at least one of the following pharmacokinetic parameters following parenterally administering over a period of about 15 minutes to about to 45 minutes to a patient: a mean peak plasma concentration ($C_{max}$) from about 750 ng/ml to about 20,300 ng/ml; an $AUC_{(0-12)}$ from about 1400 hr*ng/mL to about 55,300 hr*ng/mL; a $AUC_{last}$ from about 1300 hr*ng/mL to about 55,300 hr*ng/mL; an $AUC_{(0-inf)}$ from about 14000 hr*ng/mL to about 55,300 hr*ng/mL; or a total apparent volume of distribution ($V_{ss}$) from about 100 L to about 180 L.

12. The emulsion of claim 11, wherein the emulsion has a pH value of from about 4 to about 9.

13. The emulsion of claim 11, wherein the emulsion has a viscosity of about from about 1 cps to about 1000 cps and is filterable through a 0.2 micron filter.

14. The emulsion of claim 11, wherein the emulsion has at least one of the following characteristics: a PFAT value of less than 0.05%; a viscosity from about 1 cps to about 3 cps; a polydispersity index of about less than 0.8; a transmittance of greater than about 10%; a zeta potential in a range of −50 mV to +50 mV; a D50 of mean droplet diameter of less than 200 nm when measured at 2-8 degrees C.; 25 degrees C./60% RH and 30 degrees C. at 6 months; or both a D50 and D90 mean droplet diameter of less than 250 nm when measured 30 degrees C. at 6 months.

15. The emulsion of claim 11, wherein the celecoxib in an amount of about 0.6% w/w of the emulsion or less.

* * * * *